(12) United States Patent
Yamaguchi

(10) Patent No.: US 10,254,258 B2
(45) Date of Patent: Apr. 9, 2019

(54) DATA PROCESSING SYSTEM FOR COMPREHENSIVE TWO-DIMENSIONAL CHROMATOGRAPH

(71) Applicant: SHIMADZU CORPORATION, Kyoto-shi, Kyoto (JP)

(72) Inventor: Shinichi Yamaguchi, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 136 days.

(21) Appl. No.: 15/027,577

(22) PCT Filed: Oct. 21, 2013

(86) PCT No.: PCT/JP2013/078489
§ 371 (c)(1),
(2) Date: Apr. 6, 2016

(87) PCT Pub. No.: WO2015/059753
PCT Pub. Date: Apr. 30, 2015

(65) Prior Publication Data
US 2016/0238577 A1 Aug. 18, 2016

(51) Int. Cl.
*G01N 30/88* (2006.01)
*G01N 30/46* (2006.01)
(Continued)

(52) U.S. Cl.
CPC ........... *G01N 30/88* (2013.01); *G01N 30/463* (2013.01); *G01N 30/72* (2013.01);
(Continued)

(58) Field of Classification Search
CPC .............................. G01N 30/463; G01N 30/72
See application file for complete search history.

(56) References Cited

U.S. PATENT DOCUMENTS

2002/0148353 A1* 10/2002 Seeley ................. G01N 30/463
95/86
2005/0022168 A1* 1/2005 Zhu ......................... G06F 19/24
717/124
(Continued)

FOREIGN PATENT DOCUMENTS

JP 2001249114 A 9/2001
JP 2011-122822 A 6/2011

OTHER PUBLICATIONS

English Translation—JP2011-122822 (IDS).*
(Continued)

*Primary Examiner* — Christine A Enad
(74) *Attorney, Agent, or Firm* — Sughrue Mion, PLLC

(57) ABSTRACT

A two-dimensional chromatogram creator creates a two-dimensional chromatogram based on data collected by a comprehensive two-dimensional GC/MS analysis. An extraction condition conformity determiner determines whether or not each MS/MS spectrum obtained through the analysis conforms to a compound extraction condition previously stored in a storage section, such as the presence of a specific peak on the MS/MS spectrum. Each spectrum which conforms to the condition is extracted. This spectrum is most likely to reflect a partial structure of a compound in which an analysis operator is interested. Accordingly, a condition conformity information superposing displayer displays a marker whose appearance varies according to the compound extraction condition, at a position corresponding to the retention time of the extracted spectrum on the two-dimensional chromatogram. On this two-dimensional chromatogram, the analysis operator can intuitively understand whether or not the compound of interest is present and where this compound is located.

6 Claims, 4 Drawing Sheets

(51) Int. Cl.
*G01N 30/86* (2006.01)
*G01N 30/72* (2006.01)

(52) U.S. Cl.
CPC ..... *G01N 30/8679* (2013.01); *G01N 30/7233* (2013.01); *G01N 2030/8648* (2013.01); *G01N 2030/8804* (2013.01)

(56) References Cited

U.S. PATENT DOCUMENTS

| | | | | |
|---|---|---|---|---|
| 2006/0115904 A1* | 6/2006 | Cai | ........................ | G01N 30/463 436/161 |
| 2008/0046447 A1* | 2/2008 | Sadygov | ............ | G01N 30/8644 |
| 2009/0145203 A1* | 6/2009 | Vorm | ................ | B01D 15/1871 73/61.53 |
| 2013/0008859 A1* | 1/2013 | Witt | ..................... | G01N 30/463 210/767 |
| 2014/0298990 A1* | 10/2014 | Fan | ..................... | G01N 30/463 95/23 |

OTHER PUBLICATIONS

Written Opinion for PCT/JP2013/078489 dated Dec. 24, 2013. [PCT/ISA/237].

"GC Image GCxGC Software", [online], GC Image LLC, [accessed on Aug. 23, 2013], the Internet <URL: http://www.gcimage.com/gcxgc/index.html>.

"GCxGC System", [online], Shimadzu Corporation, [accessed on Aug. 23, 2013], the Internet <URL:http://www.an.shimadzu.co.jp/gcms/gcxgc/apl.htm>.

International Search Report for PCT/JP2013/078489 dated Dec. 24, 2013.

Communication dated Aug. 8, 2016, from the European Patent Office in counterpart European application No. 13896105.7.

* cited by examiner

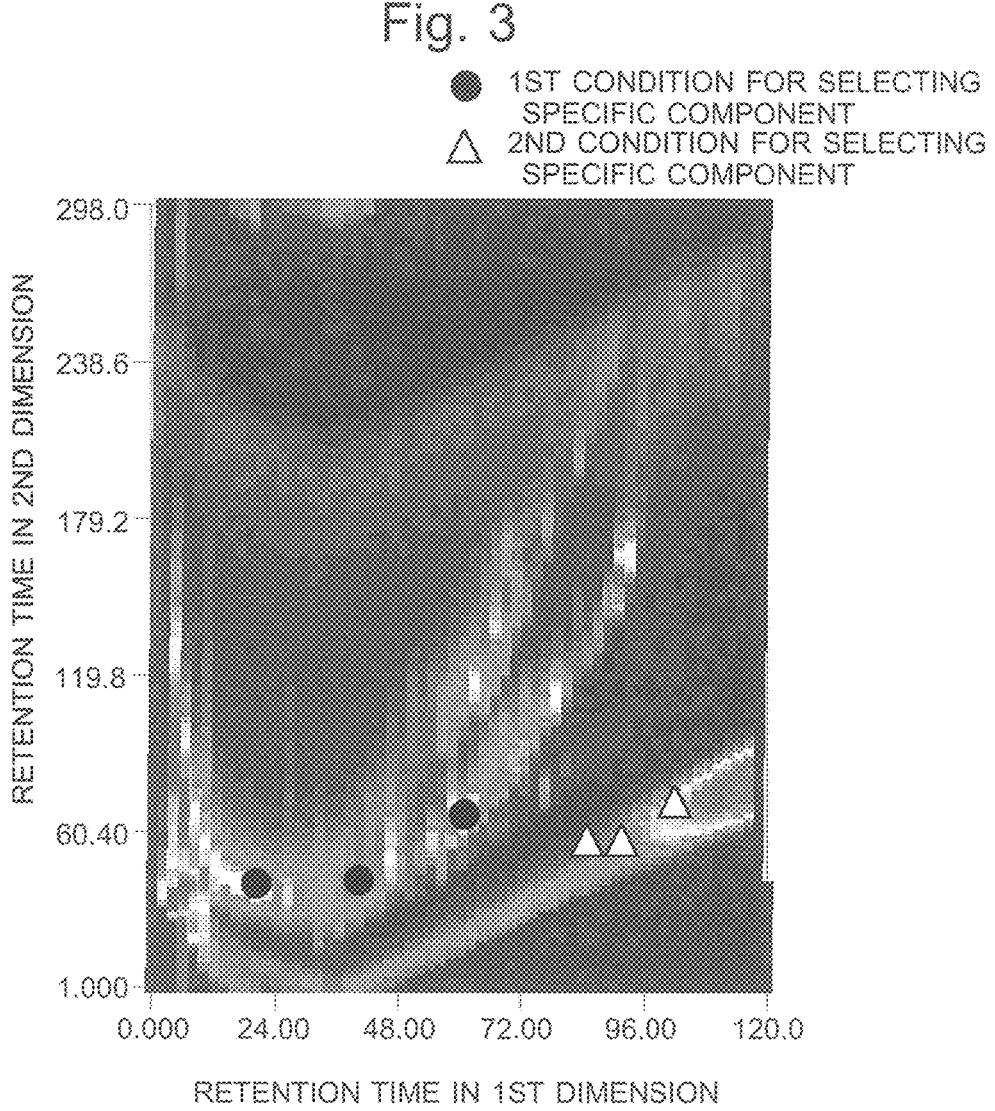

DATA PROCESSING SYSTEM FOR COMPREHENSIVE TWO-DIMENSIONAL CHROMATOGRAPH

CROSS REFERENCE TO RELATED APPLICATIONS

This application is a National Stage of International Application No. PCT/JP2013/078489 filed Oct. 21, 2013, the contents of all of which are incorporated herein by reference in their entirety.

TECHNICAL FIELD

The present invention relates to a data processing system for a comprehensive two-dimensional chromatograph used for processing data collected with a comprehensive two-dimensional gas chromatograph (GC), comprehensive two-dimensional liquid chromatograph (LC) or similar device. More specifically, it relates to a data processing system for processing and displaying data obtained with a comprehensive two-dimensional chromatograph which uses, as the detector, a mass analyzer, ion mobility spectrometer, photodiode detector, or other detectors with which a relationship between the signal intensity and a certain dimension other than the retention time (e.g. mass-to-charge ratio, migration time or wavelength) can be obtained.

BACKGROUND ART

As one technique for the gas chromatographic analysis, a technique called the "comprehensive two-dimensional GC" or "GC×GC" is commonly known (for example, refer to Patent Literature 1).

In the comprehensive two-dimensional GC, various components contained in a target sample are initially separated with a column as the first dimension (which is hereinafter called the "primary column"). The thereby eluted components are introduced into a modulator. The modulator repeats the operation of catching the introduced components at regular intervals of time (which is normally within a range from a few seconds to one dozen seconds; this interval of time is hereinafter called the "modulation time") and releasing those components with an extremely narrow time bandwidth into a column as the second dimension (which is hereinafter called the "secondary column"). In general, the component separation in the primary column is performed under such a condition that the elution occurs at a rate approximately equal to or slightly low than the rate applied in a commonly used GC. On the other hand, as compared to the primary column, the secondary column has a different polarity and a smaller inner diameter, and the component separation is performed under such a condition that each elution will be completed within the specified modulation time.

In this manner, in the comprehensive two-dimensional GC, a plurality of components which have not been separated by the primary column and whose peaks overlap each other can be separated in the secondary column, whereby the separation performance is dramatically improved as compared to normal GCs. Therefore, comprehensive two-dimensional GCs are extremely effective for an analysis of a sample which contains a number of compounds whose retention times are close to each other, such as a hydrocarbon analysis of diesel fuel.

A similar technique to the comprehensive two-dimensional GC is also known in the field of liquid chromatographic analysis, i.e. the comprehensive two-dimensional LC or LC×LC, which uses two columns having different separation characteristics. In the present description, both the comprehensive two-dimensional GC and the comprehensive two-dimensional LC are collectively called the "comprehensive two-dimensional chromatograph".

These comprehensive two-dimensional chromatographs detect the components in a sample gas or sample solution which has passed through the two columns. Therefore, the data produced by the detector is a sequence of data arranged in time-series order. Accordingly, by plotting the obtained data in order of generation, a one-dimensional chromatogram as shown in FIG. 4A can be created, which is similar to a chromatogram obtained with a normal GC, i.e. which has the horizontal axis indicating the retention time and the vertical axis indicating the signal intensity. In FIG. 4A, tm denotes the modulation time. The section of the chromatogram within this time (tm) is the chromatogram which reflects the state of separation of the components in the secondary column.

As noted earlier, in may cases, the two columns in the comprehensive two-dimensional chromatograph have different separation characteristics. Therefore, to show the state of separation in each column in an easy-to-understand form, a two-dimensional chromatogram having two orthogonal axes which respectively indicate the retention time in the primary column and the retention time in the secondary column is created, with the signal intensity represented by contour lines, color scale, or gray scale. FIG. 4B illustrates the order in which the data are arrayed to create the two-dimensional chromatogram from one-dimensional chromatogram data. The range of the vertical axis of this graph corresponds to the modulation time tm. The one-dimensional chromatogram data are sequentially plotted upward from the lower end (0) along the vertical axis (the solid arrow in FIG. 4B). After reaching tm, the plotting point is shifted rightward along the horizontal axis and returned to the lower end of the vertical axis (the broken line in FIG. 4B), after which the upward-plotting operation along the vertical axis is repeated. Consequently, a two-dimensional chromatogram as shown in FIG. 4C is obtained. In FIG. 4C, the signal intensity is indicated by contour lines.

FIG. 5 is one example of the two-dimensional chromatogram based on actually measured data in a comprehensive two-dimensional GC. In this example, the signal intensity is represented by a color scale (although the gray-scaled representation is used in the drawing, since colored drawings are not allowed). In the case of a temperature-programmed analysis in which the temperature of the columns is increased with time, the horizontal axis in the two-dimensional chromatogram represents the order of the boiling point, while the vertical axis represents the order of polarity. Therefore, the analysis operator can easily understand the nature of each component on the basis of the two-dimensional chromatogram. Even when many components are contained in the sample, the analysis operator can intuitively understand what kinds of components are contained.

As a data processing software product for creating such a two-dimensional chromatogram, the "GC Image" offered by GC Image LLC is commonly known (see Non Patent Literature 1).

As disclosed in Non Patent Literature 2, in order to identify or quantify various components in a sample which contains a comparatively high amount of foreign substances, it is useful to combine the comprehensive two-dimensional chromatograph having the previously described high level of separation performance with a mass spectrometer, and in particular, a mass spectrometer capable of MS/MS analyses, such as a triple quadrupole mass spectrometer or ion-trap time-of-flight mass spectrometer. For example, with the triple quadrupole mass spectrometer, it is possible to select, as the precursor ion, an ion having a specific mass-to-charge ratio originating from a compound, fragment the precursor ion by a collision induced dissociation process, and perform an exhaustive detection (i.e. scan measurement) of various product ions produced by the fragmentation. This is the MS/MS analyzing technique called the "product ion scan measurement". By this technique, fragments (ion species) which result from the breakage of the bonds at various sites on a specific chemical structure can be investigated.

FIG. 6 shows one example of the MS/MS spectrum obtained by the product ion scan measurement. In FIG. 6, the peak of the precursor ion, which actually cannot be detected, is shown in the broken line.

Additionally, the triple quadrupole mass spectrometer is capable of performing other MS/MS analysis techniques, such as a precursor ion scan measurement for exhaustively investigating precursor ions which produce a specific kind of product ion, or a neutral loss scan measurement for investigating the combination of the precursor ion and product ion which produce a specific kind of electrically neutral fragment ("neutral loss") through the fragmentation.

Accordingly, as in the case of screening drugs or poisons, when a large number of compounds which have comparatively similar chemical structures (e.g. which have the same basic skeleton and merely differ from each other in the kind of substituent group) need to be simultaneously identified, it is preferable to use a comprehensive two-dimensional chromatograph having a triple quadrupole mass analyzer as its detector in such a manner that, after the large number of compounds are sufficiently separated in the temporal direction as well as according to their mass-to-charge ratios, the product ion scan measurement or neutral loss scan measurement is performed, and the thereby collected data are analyzed and processed to discern the difference in their partial chemical structure.

In recent years, MS/MS analyses in triple quadrupole mass spectrometers or ion-trap time-of-flight mass spectrometers have become increasingly faster in operation and more complex in procedure. For example, there is an apparatus having the function of: automatically determining the mass-to-charge ratio, signal intensity and other properties of a peak which has appeared on a measured mass spectrum; automatically selecting a precursor ion which conforms to a predetermined condition; and performing a product ion scan measurement for the selected ion, instead of a product ion scan measurement for a precursor ion having a previously specified mass-to-charge ratio. Such a function is commonly known as the IDA (intelligent data acquisition, information-dependent acquisition, etc.), auto-MS/MS, or by other names.

CITATION LIST

Patent Literature

Patent Literature 1: JP 2011-122822 A

Non Patent Literature

Non Patent Literature 1: "GC Image GCxGC Software", [online], GC Image LLC, [accessed on Aug. 23, 2013], the Internet Non Patent Literature 2: "GCxGC System", [online], Shimadzu Corporation, [accessed on Aug. 23, 2013], the Internet

SUMMARY OF INVENTION

Technical Problem

In an analysis using the previously described comprehensive two-dimensional chromatograph triple quadrupole mass spectrometer, a number of MS/MS spectra, which may possibly amount to several thousands, are obtained in addition to the comprehensive two-dimensional chromatogram, e.g. the one shown in FIG. 5. Additionally, in the case where the previously described IDA or similar function for automatically obtaining an MS/MS spectrum is used, the analysis operator is not informed of the exact mass-to-charge ratio of the precursor ion for which the MS/MS spectrum has been obtained. Therefore, even the simple task of finding the MS/MS spectrum which contains the structured information of the targeted compound is cumbersome and time-consuming for the analysis operator. Furthermore, even when the analysis operator visually checks the two-dimensional chromatogram and the individual spectra, it is considerably difficult to understand the result, such as the presence or absence of a compound having the partial chemical structure in which the analysis operator is interested.

The present invention has been developed in view of such problems. Its primary objective is to provide a data processing system for a comprehensive two-dimensional chromatograph which allows an analysis operator to intuitively obtain useful information for the identification or structural analysis of a compound, such as the presence of a compound in which the analysis operator is interested or a compound including a chemical structure in which the analysis operator is interested, or an outline of the relationship among the retention times of the compounds when there are a plurality of compounds of interest.

Solution to Problem

The present invention developed for solving the previously described problem is a data processing system for a comprehensive two-dimensional chromatograph for processing data collected with a comprehensive two-dimensional chromatograph in which a sample separated into components by a primary column is divided at predetermined intervals of time, the divided sample is introduced into a secondary column to be further separated into components, and the components are introduced into a detector to be individually detected, the data processing system including:

a) a chromatogram creator for creating a two-dimensional chromatogram with two axes respectively indicating the retention time in the primary column and the retention time in the secondary column, based on the data collected with the comprehensive two-dimensional chromatograph;

b) a condition entry-and-setting section for allowing an analysis operator to enter and set an extraction condition for selecting a piece of characteristic data from the data collected with the comprehensive two-dimensional chromatograph; and c) a superposing display processor for determining whether or not each piece of data collected with the comprehensive two-dimensional chromatograph conforms to the extraction condition entered and set through the condition entry-and-setting section, and for displaying a predetermined marker in a superposed form on the two-dimensional chromatogram if a piece of data which conforms to the condition is present, the marker displayed at a position corresponding to the retention times at which that piece of data is obtained.

The "comprehensive two-dimensional chromatograph" may be either a comprehensive two-dimensional gas chromatograph or comprehensive two-dimensional liquid chromatograph.

In the data processing system according to the present invention, the analysis operator enters and sets an extraction condition, such as a piece of data characteristic of the compound of interest e.g. a characteristic pattern of the signal intensity), using the condition entry-and-setting section in advance (i.e. before the execution of an analysis using the comparative two-dimensional chromatograph) or prior to the data analysis process after the data collection. The condition entry-and-setting section allows the entry and setting of extraction conditions for selecting a plurality of different kinds of characteristic data.

The superposing display processor determines, for each piece of data sequentially obtained with the passage of time by the comprehensive two-dimensional chromatograph, whether or not the piece of data conforms to the extraction condition. If a piece of data which conforms to the condition has been found, the superposing display processor locates the retention time at which that piece of data has been obtained, and displays the predetermined marker in a superposed form at a position corresponding to that retention time on the two-dimensional chromatogram. Accordingly, the analysis operator can visually recognize the retention time at which the compound which satisfies the extraction condition set by the analysis operator appears on the two-dimensional chromatogram. If there are a plurality of compounds which satisfy the extraction condition, the same marker is displayed at a plurality of positions on the two-dimensional chromatogram, so that the analysis operator at a glance can understand the result, such as the relationship among the retention times of those compounds.

The superposing display processor may be configured so that, when a plurality of extraction conditions are set by the condition entry-and-setting section, it applies each individual extraction condition to determine whether or not the collected data conform to the extraction condition, and if a piece of data which conforms to one extraction condition is found, it displays the marker in a shape (or color, etc.) which varies according to that extraction condition on the two-dimensional chromatogram.

As one mode of the data processing system for a comprehensive two-dimensional chromatograph according to the present invention, the detector may be a detector which repeatedly acquires a signal intensity with a change in a third dimension which is the mass-to-charge ratio, wavelength, or time other than the retention time, and the extraction condition may include a value related to the third dimension. Specifically, when a mass spectrometer is used as the detector, the third dimension is the mass-to-charge ratio. When an ultraviolet-visible spectrometric detector, photodiode detector, fluorometric detector or similar device is used as the detector, the third dimension is the wavelength. When an ion mobility spectrometer or similar device is used as the detector, the third dimension is the time.

In any case, the third dimension is an element by which different components can be separated. Accordingly, even if a plurality of components in a sample have not been sufficiently separated by the two columns, the plurality of mutually superposed components can be separated by the third dimension when they are detected in the detector.

As one typical embodiment, the detector may be a mass spectrometer capable of an $MS^n$ analysis (where n is an integer equal to or greater than two), and the extraction condition may be a condition for making a determination on information extracted from spectrum data obtained by an $MS^n$ analysis performed using the mass spectrometer.

For example, the mass spectrometer may be a triple quadrupole mass spectrometer or ion-trap time-of-flight mass spectrometer, in which case it is possible to repeat an $MS^1$ analysis (the normal mass spectrometry which includes no ion fragmentation) and an $MS^2$ analysis according to a previously set measurement condition, or to repeat an automatic $MS^2$ analysis in which an $MS^2$ analysis is automatically performed when a certain condition is satisfied according to the result (mass spectrum) of an $MS^1$ analysis. In these cases, for example, a plurality of spectra of the product ions which are generated by the fragmentation of a specific precursor ion, or a plurality of spectra of the precursor ions from which a specific product ion is generated are obtained, depending on the content of the measurement condition. Accordingly, by setting an appropriate extraction condition (e.g. a peak should be observed at a specific mass-to-charge ratio on the spectrum, or a specific neutral loss corresponding to the difference in the mass-to-charge ratio from the precursor ion should be observed), the elution position of a compound having a partial chemical structure of interest can be displayed on the two-dimensional chromatogram.

Advantageous Effects of the Invention

With the data processing system for a comprehensive two-dimensional chromatograph according to the present invention, the elution position of a compound from which a piece of data that satisfies the condition entered and set by an analysis operator is displayed in a superposed form on a two-dimensional chromatogram, so that the analysis operator can at a glance ascertain whether or not the sample contains a compound of interest or a compound including a chemical structure of interest. When there are a plurality of compounds of interest, the analysis operator can intuitively obtain useful information, such as an outline of the relationship among the elution positions (i.e. retention times) of those compounds, in relation to the distribution of the two-dimensional peaks on the two-dimensional chromatogram.

BRIEF DESCRIPTION OF DRAWINGS

FIG. 3 is one example of the two-dimensional chromatogram displayed in the comprehensive two-dimensional GC system of the present embodiment.

DESCRIPTION OF EMBODIMENTS

Figure 1:
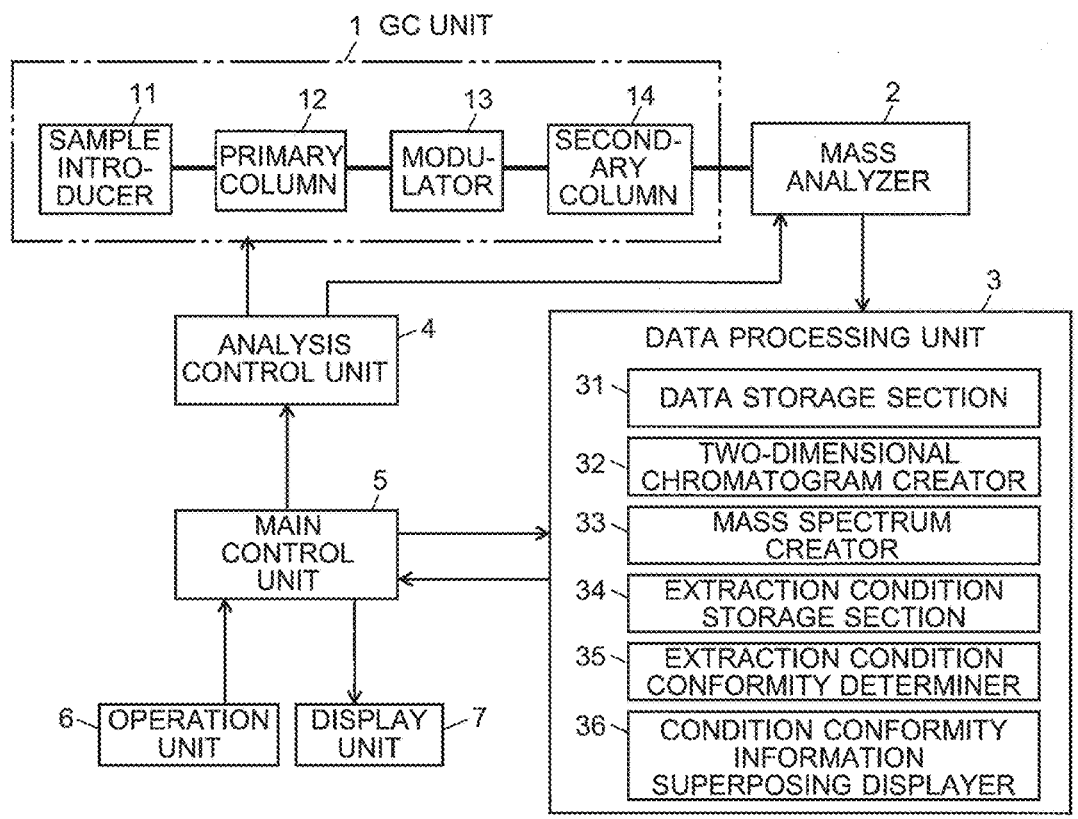
FIG. 1 is a schematic configuration diagram of one embodiment of the comprehensive two-dimensional GC system equipped with a data processing system for a comprehensive two-dimensional chromatograph according to the present invention.
Figure 2:
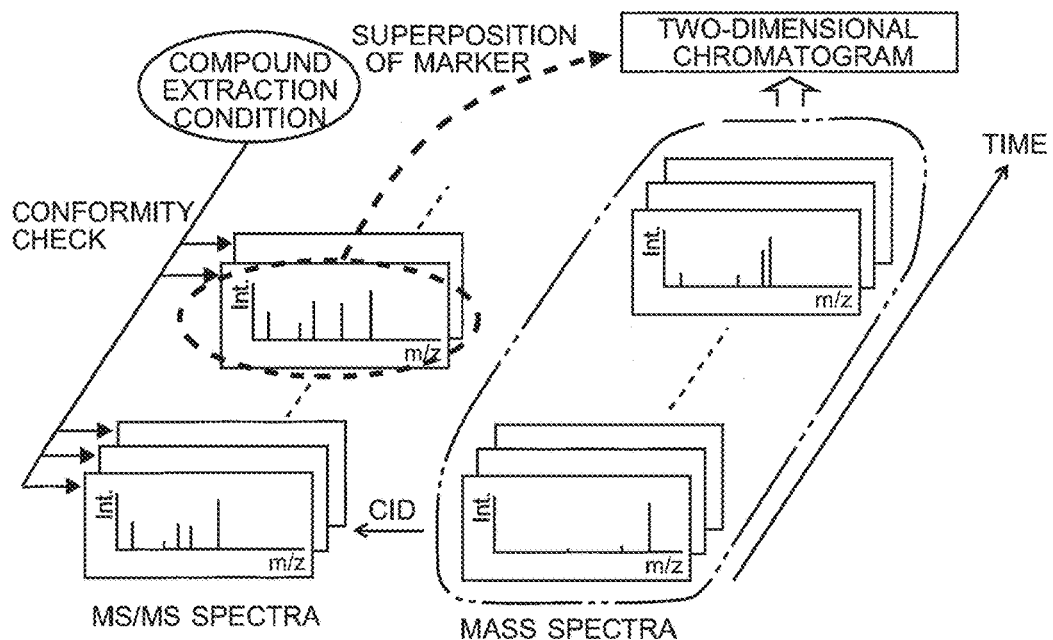
FIG. 2 is a diagram illustrating the displaying process in the comprehensive two-dimensional GC system of the present embodiment.

One embodiment of the comprehensive two-dimensional GC system using a data processing system for a comprehensive two-dimensional chromatograph according to the present invention is hereinafter described with reference to the attached drawings. FIG. 1 is a schematic configuration diagram of the comprehensive two-dimensional GC system according to the present embodiment, FIG. 2 is a diagram illustrating the displaying process in the comprehensive two-dimensional GC system of the present embodiment, and FIG. 3 is one example of the two-dimensional chromatogram displayed in the comprehensive two-dimensional GC system of the present embodiment.

In the comprehensive two-dimensional GC system of the present embodiment, a GC unit 1 includes: a primary column 12; a sample introducer 11 including a sample vaporization chamber and other elements for introducing sample gas into the primary column 12; a modulator 13 for catching eluted components (compounds) from the primary column 12 at regular intervals of time (modulation time, tm) and for sending them out in a temporally compressed form; and a secondary column 14 capable of high-speed separation with the separation characteristics different from those of the primary column 12 (typically, with a different polarity). The sample gas containing the components separated by the secondary column 14 is introduced into a mass analyzer 2 capable of $MS^n$ analyses. The mass spectrometer 2 produces detection signals corresponding to the compounds, which are sequentially sent to a data processing unit 3.

Though not shown, the mass analyzer 2 is a triple quadrupole type mass analyzer having a quadrupole mass filter placed on each of the front and rear sides of a collision cell. An ion having a specific mass-to-charge ratio (precursor ion) selected by the front quadrupole mass filter is fragmented within the collision cell by a collision induced dissociation process. Among the various product ions produced by the process, an ion having a specific mass-to-charge ratio can be selected by the rear quadrupole mass filter.

The data processing unit 3 includes the following functional blocks: a data storage section 31 for collecting and storing data sequentially fed from the mass analyzer 2 with the passage of time in the previously described manner; a two-dimensional chromatogram creator 32 for creating a two-dimensional chromatogram based on the data stored in the data storage section 31; a mass spectrum creator 33 for creating mass spectra (including MS/MS spectra) based on the data stored in the data storage section 31; an extraction condition storage section 34 for storing a compound extraction condition entered and set by an analysis operator; an extraction condition conformity determiner 35 for searching each mass spectrum for a peak, a mass difference between the peaks, or other features which conform to the compound extraction condition stored in the extraction condition storage section 34 and for extracting a mass spectrum which conforms to the condition; and a condition conformity information superposing displayer 36 for displaying, in a superposed form on the two-dimensional chromatogram, a marker at a position corresponding to the time at which the mass spectrum extracted by the extraction condition conformity determiner 35 was obtained.

The operation of each section in the GC unit 1 and that of the mass analyzer 2 are controlled by an analysis control unit 4. The main control unit 5, to which an operation unit 6 and display unit 7 as the user interfaces are connected, is responsible for the input-output controls as well as the general control of the system. The main control unit 5, analysis control unit 4 and data processing unit 3 can be embodied by using a personal computer as hardware resources, with their respective functions realized by running, on that personal computer, a dedicated controlling and processing software program previously installed on the same computer.

An analysis operation for a sample performed by the GC unit 1 and the mass analyzer 2, i.e. the data collection operation performed in the present comprehensive two-dimensional GC system is schematically described.

In the GC unit 1, the sample introducer 11 responds to a command from the analysis control unit 4 and introduces a sample to be analyzed into carrier gas being supplied to the primary column 12 at a substantially constant flow rate. Normally, this sample contains a number of compounds. While passing through the primary column 12 which is temperature-controlled according to a predetermined temperature-increasing program, those various compounds contained in the sample are separated, to be eluted in a temporally shifted fashion. At this point, it is not always the case that all compounds are sufficiently separated; compounds whose retention times in the primary column 12 are close to each other will be eluted in a mutually overlapped (mixed) form.

The modulator 13 repeats the operation of entirely catching the compounds eluted from the primary column 12 within the modulation time tm and sending them into the secondary column 14 in a temporally compressed form with an extremely narrow bandwidth. Accordingly, the compounds eluted from the primary column 12 are entirely sent into the secondary column 14. While passing through the secondary column 14, the compounds sent into this column at regular intervals of time defined by the modulation time tm are temporally separated at a high level of resolution and eluted, to be eventually introduced into the mass analyzer 2 in order of elution.

Figure 4A:
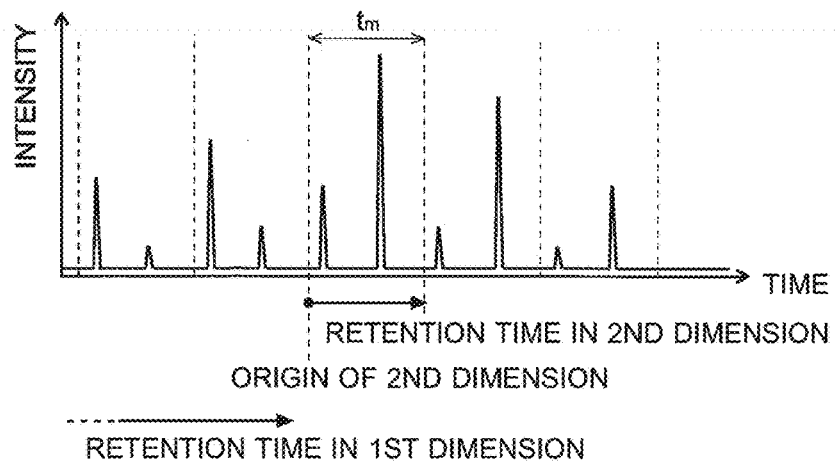
FIG. 4A is one example of the one-dimensional chromatogram based on the data collected with a comprehensive two-dimensional GC.

When a scan measurement is performed in a normal mode, i.e. with no fragmentation of the ions within the collision cell in the mass analyzer 2 (normally, the ion selection is only performed in the rear quadrupole mass filter; no ion selection is performed in the front quadrupole mass filter), mass spectrum data covering a predetermined mass-to-charge-ratio range are successively obtained with the passage of time (see FIG. 2). The data storage section 31 in the data processing unit 3 collects and stores those mass spectrum data sequentially obtained with the passage of time. For each scan measurement, an ion intensity signal is obtained by totaling the obtained ion intensities. By arraying the ion intensity signals in the time-series order, a one-dimensional total ion chromatogram as shown in FIG. 4A can be created.

If the compound contained in the sample has a comparatively complex chemical structure, there may be a structural isomer, positional isomer or other variations having the same molecular weight yet different chemical structures. In such a case, the identification of the compounds requires investigating a fragment structure of the compound. To this end, an MS/MS ($=MS^2$) analysis, such as the product ion scan measurement, precursor ion scan measurement or neutral loss scan measurement is performed.

For example, in the case where a product ion scan measurement for a specific precursor ion is to be repeatedly performed over a predetermined range of measurement time (which may naturally be the entire range of the measurement time), the analysis operator using the operation unit 6 previously sets the measurement conditions (e.g. the mass-to-charge ratio of the precursor ion as the target, and the range of measurement time) and commands the initiation of the analysis. Then, the analysis control unit 4 controls the mass analyzer 2 so as to perform the MS/MS analysis according to the set measurement conditions. As a result, the product ion scan measurement with the set ion as the precursor ion is repeatedly performed during the set range of measurement time, and one set of MS/MS spectrum data is obtained for each repetition of the measurement.

In the case of using the automatic MS/MS function, the analysis operator using the operation unit 6 previously sets the condition for the precursor ion selection (e.g. the threshold of the signal intensity) instead of setting the mass-to-charge ratio of the precursor ion. Only when an ion which conforms to the precursor ion selection condition that has been set is detected on the mass spectrum obtained by a normal scan measurement, the mass analyzer 2 repeatedly performs the product ion scan measurement, with the detected ion set as the precursor ion, a predetermined number of times subsequently to the scan measurement.

In any case, when an MS/MS (=$MS^2$) analysis, such as a product ion scan measurement, precursor ion scan measurement or neutral loss scan measurement is performed, MS/MS spectra over a predetermined mass-to-charge-ratio range are obtained in addition to the mass spectrum data FIG. 2). Those MS/MS spectrum data obtained in this manner with the passage of time are also stored in the data storage section 31 along with the mass spectrum data.

After one sequence of the comprehensive two-dimensional GC/MS analysis for the sample is completed in the previously described manner, or at an appropriate point in time before the execution of the analysis, the analysis operator performs predetermined operations on the operation unit 6 to set a compound extraction condition for the compound of interest to be displayed in a superposed form on the two-dimensional chromatogram. As the compound extraction condition, various values related to the mass spectra or MS/MS spectra can be used; specific examples include the value of the mass-to-charge ratio of one or more peaks to be observed on the MS/MS spectra, the lower limit of the signal intensity of those peaks, and the value of the neutral loss corresponding to the mass difference from the precursor ion on the MS/MS spectra. It should be noted that not only a single compound extraction condition but also a plurality of compound extraction conditions can be set. The set compound extraction conditions are stored in the extraction condition storage section 34.

Figure 4B:
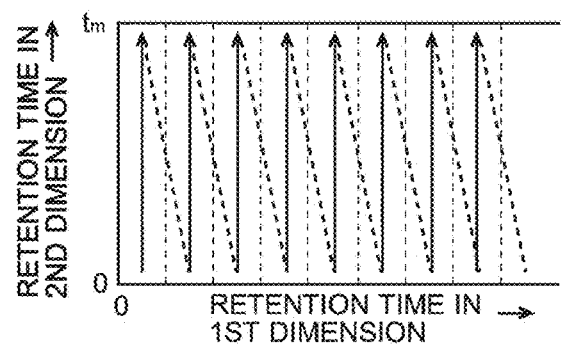
FIG. 4B is a diagram illustrating the data arrangement for creating a two-dimensional chromatogram based on the one-dimensional chromatogram.
Figure 4C:
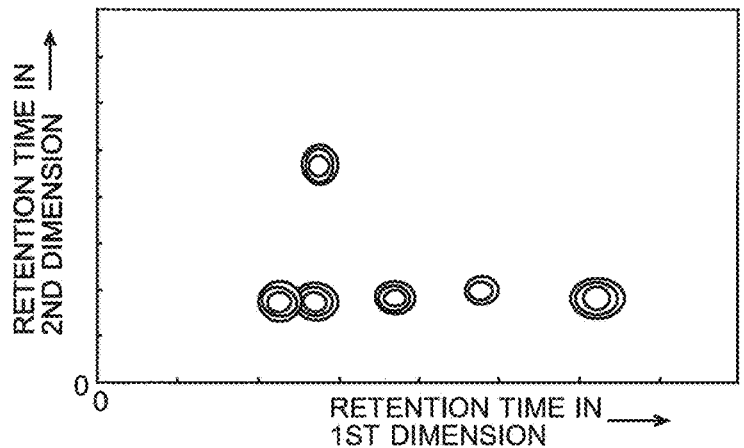
FIG. 4C is one example of the two-dimensional chromatogram.
Figure 5:
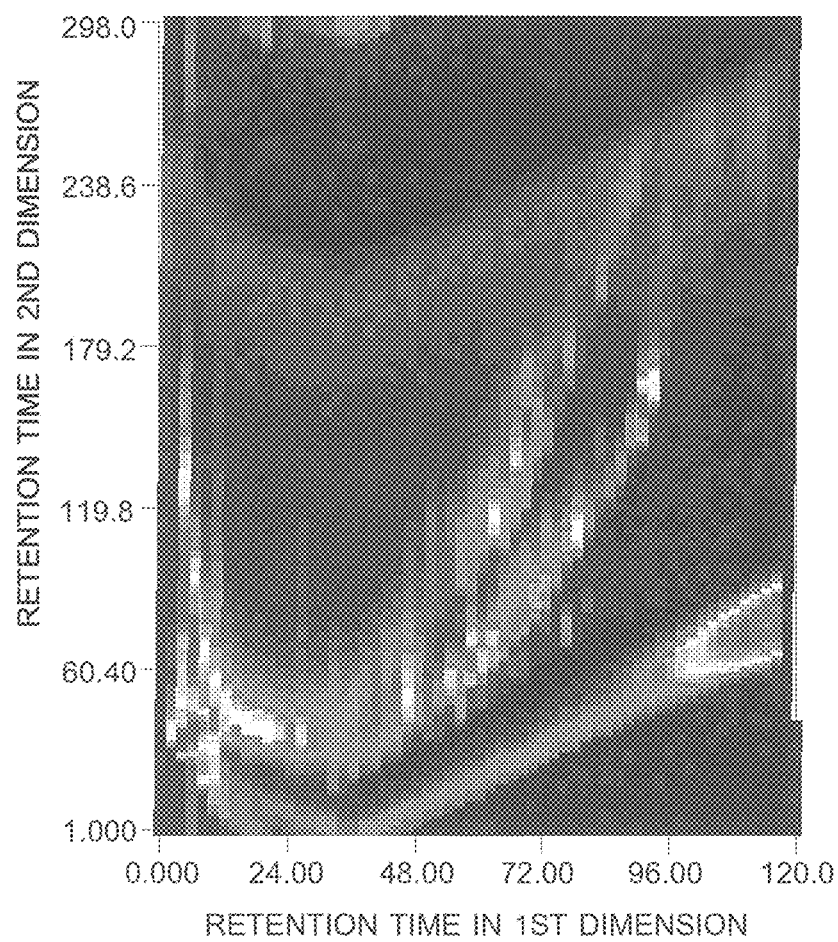
FIG. 5 is one example of the two-dimensional chromatogram in a commonly used comprehensive two-dimensional GC.
Figure 6:
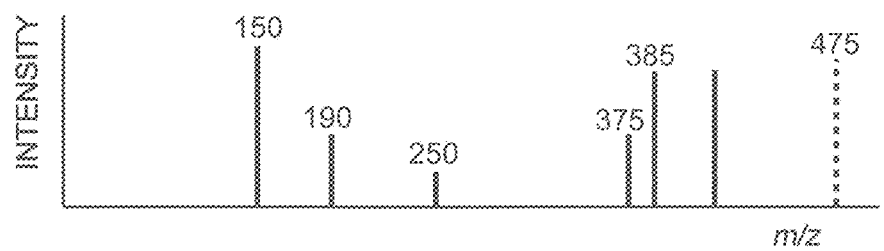
FIG. 6 is one example of the MS/MS spectrum obtained by a product ion scan measurement.

With the compound extraction condition set, when the analysis operator performs a predetermined operation for displaying the chromatogram, the two-dimensional chromatogram creator 32 reads all mass spectrum data from the data storage section 31, calculates the total value of the ion intensities for each point in time of the measurement, i.e. for each mass spectrum, and creates a two-dimensional total ion chromatogram as shown in FIG. 4B with the horizontal axis indicating the retention time in the primary column 12 and the vertical axis indicating the retention time in the secondary column 14, on which the total value of the ion intensities (signal intensity) is represented by a color scale. This is a conventionally practiced process and can be realized using an existing software product, such as the aforementioned "GC Image". As a result, a two-dimensional chromatogram as shown in FIG. 3 or FIG. 4C is created.

After the creation of the chromatogram, or in parallel with the creation of the chromatogram, the mass spectrum creator 33 reads the mass spectrum data and/or MS/MS spectrum data from the data storage section 31, and creates mass spectra and/or MS/MS spectra. The extraction condition conformity determiner 35 reads the compound extraction condition stored in the extraction condition storage section 34 and determines whether or not a peak (or other features) which conforms to the compound extraction condition is present in each mass spectrum or MS/MS spectrum, as shown in FIG. 2. Each mass spectrum or MS/MS spectrum in which a peak (or other features) which conforms to the compound extraction condition has been observed is extracted as a spectrum which originates from the compound in which the analysis operator is interested, i.e. in which the structural information of the compound of interest is reflected. When a plurality of compound extraction conditions are set, the extraction of the mass spectrum or MS/MS spectrum which conforms to the condition is performed for each compound extraction condition.

The condition conformity information superposing displayer 36 locates the retention time (the retention time in the primary column 12 and the retention time in the secondary column 14) corresponding to each mass spectrum or MS/MS spectrum extracted by the extraction condition conformity determiner 35. Subsequently, it superposes a marker at each of the located retention times on the two-dimensional chromatogram created by the two-dimensional chromatogram creator 32, with the appearance of the marker (shape, color, etc.) changed according to the compound extraction condition. The two-dimensional chromatogram with the markers superposed is displayed via the main control unit 5 on the screen of the display unit 7.

As a result, for example, a two-dimensional chromatogram as shown in FIG. 3 is displayed on the screen of the display unit 7. In FIG. 3, two types of markers represented by the filled circle and white triangle, which respectively correspond to two kinds of compound extraction conditions, are displayed in a superposed form on the two-dimensional chromatogram. On this display, the analysis operator can easily locate the retention times at which the compounds that conform to the compound extraction conditions specified by the analysis operator appear. Furthermore, the analysis operator can intuitively understand the relationship among the retention times of a plurality of compounds that conform to one compound extraction condition.

In the example of FIG. 3, the signal intensity is represented by a color scale (in the drawing, the gray-scaled representation is used, since colored presentations are not allowed). It is also possible to display the markers in a superposed form on a two-dimensional chromatogram in which the signal intensity is represented by contour lines.

In the previously described embodiment, the two-dimensional chromatogram is created from the total ion chromatogram based on the result of a normal mode of mass spectrometry. It is also possible to create a two-dimensional chromatogram based on the data prepared by performing a predetermined process on each of the mass spectra obtained through the repetition of a normal mode of mass spectrometry. For example, the two-dimensional chromatogram may be created using the mass spectra after narrowing the number of ions in each mass spectrum by performing a mass defect filtering process which selects only such ions whose mass-to-charge ratios after the decimal point are close to those of the ions originating from a certain substance. For example, in the case where an unexpected metabolite is produced from a certain substance, this technique is effective for detecting an ion of metabolite origin with a high level of sensitivity while removing the influence of foreign substances. The two-dimensional chromatogram may also be created using the mass spectra after narrowing the number of ions in each mass spectrum by performing, on each of the mass spectra obtained through the repetition of a normal mode of mass spectrometry, an isotopic filtering process in which ions are selected based on the intensity ratio between the monoisotopic ion peak and an isotopic ion peak. This technique is effective for the high-sensitivity detection of an ion originating from a specific substance labeled with a labeling reagent, such as deuterium or carbon isotopes ($^{13}C$ or $^{14}C$).

Additionally, for example, in the case where an MS/MS analysis is repeatedly performed from the beginning point to the ending point of the measurement, the two-dimensional chromatogram may be created from a total ion chromatogram based on the result of the MS/MS analysis (e.g. a chromatogram based on the total value of the ion intensifies in the product ion spectrum within a predetermined mass-to-charge-ratio range). In this case, instead of creating the two-dimensional chromatogram from simple MS/MS spectra (i.e. the spectra which entirely reflect the obtained data without omission), the two-dimensional chromatogram may be created using only a limited set of spectrum data obtained by extracting a peak having a specific mass-to-charge ratio or a peak corresponding to a specific neutral loss, or by performing a narrowing process using various kinds of filters (e.g. the previously described mass defect filter). The two-dimensional chromatogram may also be created from spectra based on the similarity, difference or other relationships among the MS/MS spectra. In summary, the information represented by the value of the signal intensity of the two-dimensional chromatogram may be any type of information as long as the chromatogram is created on the basis of mass spectrum data or MS/MS spectrum data obtained by a comprehensive two-dimensional GC/MS analysis performed on a sample.

In the previous embodiment, a triple quadrupole mass analyzer is used as the detector for the comprehensive two-dimensional chromatograph. However, the present invention can also be applied in a comprehensive two-dimensional chromatograph using a detector other than a mass analyzer.

For example, in a comprehensive two-dimensional LC, a photodiode detector or similar device may be used as the detector. With such a detector, the signal intensity (e.g. absorbance) over a predetermined wavelength range can be repeatedly obtained. Accordingly, for example, by previously setting an appropriate compound extraction condition (e.g. a peak should be present at a specific wavelength) and extracting a wavelength spectrum which conforms to that compound extraction condition, the marker can be displayed in the previously described manner on the two-dimensional chromatogram at the position (retention time) of the compound in which the analysis operator is interested.

In a comprehensive two-dimensional GC having an ion mobility spectrometer placed between the GC unit and the mass analyzer, a set of data showing the relationship between the migration time and the signal intensity can be collected in the ion mobility spectrometer. Accordingly, for example, by previously setting an appropriate compound extraction condition (e.g. a peak should be present at a specific migration time on the spectrum showing the relationship between the migration time and the signal intensity) and extracting a spectrum which conforms to that compound extraction condition, the marker can be displayed in the previously described manner on the two-dimensional chromatogram at the position (retention time) of the compound in which the analysis operator is interested. It is also possible to display both the marker based on the result obtained with the ion mobility spectrometer and the marker based on the result obtained with the mass analyzer in a superposed form on one two-dimensional chromatogram.

Additionally, it should be noted that the previously described embodiment and the previously described variations are mere examples of the present invention, and any change, modification, or addition appropriately made within the spirit of the present invention will evidently fall within the scope of claims of the present application.

REFERENCE SIGNS LIST

1 . . . GC Unit
11 . . . Sample Introducer
12 . . . Primary Column
13 . . . Modulator
14 . . . Secondary Column
2 . . . Mass Analyzer
3 . . . Data Processing Unit
4 . . . Analysis Control Unit
5 . . . Main Control Unit
6 . . . Operation Unit
7 . . . Display Unit
31 . . . Data Storage Section
32 . . . Two-Dimensional Chromatogram Creator
33 . . . Mass Spectrum Creator
34 . . . Extraction Condition Storage Section
35 . . . Extraction Condition Conformity Determiner
36 . . . Condition Conformity Information Superposing Displayer

The invention claimed is:

1. A data processing system for a comprehensive two-dimensional chromatograph for processing data collected with a comprehensive two-dimensional chromatograph in which a sample separated into components by a primary column is divided at predetermined intervals of time, the divided sample is introduced into a secondary column to be further separated into components, and the components are introduced into a detector to be individually detected, the data processing system comprising:

a) a processor configured to execute processor-executable instructions comprising a chromatogram creator for creating a two-dimensional chromatogram with two axes respectively indicating a retention time in the primary column and a retention time in the secondary column, based on the data collected with the comprehensive two-dimensional chromatograph;

b) an operation interface comprising a condition entry-and-setting section for allowing an analysis operator to enter and set an extraction condition, the extraction condition being used for selecting a piece of characteristic data from the data collected with the comprehensive two-dimensional chromatograph after passing the second column; and c) a superposing display processor for determining whether or not each piece of data collected with the comprehensive two-dimensional chromatograph conforms to the extraction condition entered and set through the condition entry-and-setting section, and for displaying a predetermined marker in a superposed form on the two-dimensional chromatogram if a piece of data which conforms to the condition is present, the marker displayed at a position corresponding to the retention times at which that piece of data is obtained, whereby the analysis operator can at a glance ascertain whether or not the sample contains a compound of interest or a compound including a chemical structure of interest.

2. The data processing system for a comprehensive two-dimensional chromatograph according to claim 1, wherein:
the detector is a detector which repeatedly acquires a signal intensity with a change in a third dimension which is a mass-to-charge ratio, wavelength, or time other than the retention time; and
the extraction condition includes a value related to the third dimension.

3. The data processing system for a comprehensive two-dimensional chromatograph according to claim 2, wherein:
the condition entry-and-setting section allows entry and setting of extraction conditions for selecting a plurality of different kinds of characteristic data; and
when a plurality of extraction conditions are set by the condition entry-and-setting section, the superposing display processor applies each individual extraction condition to determine whether or not the collected data conform to the extraction condition, and if a piece of data which conforms to one extraction condition is found, the superposing display processor displays the marker with an appearance which varies according to that extraction condition on the two-dimensional chromatogram.

4. The data processing system for a comprehensive two-dimensional chromatograph according to claim 2, wherein:
the detector is a mass spectrometer capable of an $MS^n$ analysis (where n is an integer equal to or greater than two), and the extraction condition is a condition for making a determination on information extracted from spectrum data obtained by an $MS^n$ analysis performed using the mass spectrometer.

5. The data processing system for a comprehensive two-dimensional chromatograph according to claim 4, wherein:
the condition entry-and-setting section allows entry and setting of extraction conditions for selecting a plurality of different kinds of characteristic data; and
when a plurality of extraction conditions are set by the condition entry-and-setting section, the superposing display processor applies each individual extraction condition to determine whether or not the collected data conform to the extraction condition, and if a piece of data which conforms to one extraction condition is found, the superposing display processor displays the marker with an appearance which varies according to that extraction condition on the two-dimensional chromatogram.

6. The data processing system for a comprehensive two-dimensional chromatograph according to claim 1, wherein:
the condition entry-and-setting section allows entry and setting of extraction conditions for selecting a plurality of different kinds of characteristic data; and
when a plurality of extraction conditions are set by the condition entry-and-setting section, the superposing display processor applies each individual extraction condition to determine whether or not the collected data conform to the extraction condition, and if a piece of data which conforms to one extraction condition is found, the superposing display processor displays the marker with an appearance which varies according to that extraction condition on the two-dimensional chromatogram.

* * * * *